United States Patent [19]

Cymbaluk et al.

[11] Patent Number: 5,523,512
[45] Date of Patent: Jun. 4, 1996

[54] COPPER (I) CARBOXYLATE-CONTAINING OLEFIN COMPLEXING REAGENTS

[75] Inventors: Ted H. Cymbaluk, Seabrook, Tex.; Gerhard P. Nowack; Marvin M. Johnson, both of Bartlesville, Okla.

[73] Assignee: Phillips Petroleum Company, Bartlesville, Okla.

[21] Appl. No.: 82,223

[22] Filed: Jun. 24, 1993

Related U.S. Application Data

[62] Division of Ser. No. 816,425, Dec. 31, 1991, Pat. No. 5,259,986.

[51] Int. Cl.[6] .................................................. C07C 7/148
[52] U.S. Cl. ............................................ 585/848; 585/864
[58] Field of Search .................................... 585/848, 864

[56] References Cited

U.S. PATENT DOCUMENTS

| | | | |
|---|---|---|---|
| 2,589,960 | 3/1952 | Ray | 260/677 |
| 2,900,347 | 8/1959 | Foreman | 252/182 |
| 2,943,060 | 6/1960 | Smith | 252/182 |
| 3,284,530 | 11/1966 | Nölken et al. | 260/677 |
| 3,514,488 | 5/1970 | Uobele et al. | 260/677 |
| 3,517,080 | 6/1970 | Beckham et al. | 260/677 |
| 3,517,081 | 6/1970 | Beckham et al. | 260/677 |
| 3,518,322 | 6/1970 | Beckham et al. | 260/674 |
| 3,630,676 | 12/1971 | Davis et al. | 23/204 |
| 3,754,047 | 8/1973 | Long et al. | 260/677 |
| 4,025,574 | 5/1977 | Tabler et al. | 260/677 |
| 4,102,802 | 7/1978 | Johnson et al. | 252/184 |
| 4,106,917 | 8/1978 | Fields et al. | 55/31 |
| 4,129,605 | 12/1978 | Tabler et al. | 260/669 |
| 4,398,052 | 8/1983 | Tabler et al. | 585/845 |
| 4,400,564 | 8/1983 | Johnson et al. | 585/845 |
| 5,104,570 | 4/1992 | Cymbaluk et al. | 252/182.12 |
| 5,191,153 | 3/1993 | Cymbaluk et al. | 585/833 |

OTHER PUBLICATIONS

Comprehensive Inorganic Chemistry, vol. 1, edited by J. C. Bailer, Jr., H. J. Emeleus, Sir Ronald Nyholm, & A. F. Trottman–Dickenson; p. 963 (year unavailable).
Comprehensive Inorganic Chemistry. vol. III; p. 31–32 (year unavailable).
A Comprehensive Treatise on Inorganic and Theoretical Chemistry vol. III, p. 158, by J. W. Mellor (year unavail.).

*Primary Examiner*—Anthony McFarlane
*Assistant Examiner*—Nhat D. Phan
*Attorney, Agent, or Firm*—Beverly M. Dollar

[57] ABSTRACT

Complexing reagents are provided which comprise Cu(I) carboxylates or Cu(I) sulfonates and high molecular weight olefins. The invention complexing reagents are useful for separating olefins from mixtures of olefins and paraffins.

5 Claims, 4 Drawing Sheets

COPPER (I) CARBOXYLATE-CONTAINING OLEFIN COMPLEXING REAGENTS

CROSS-REFERENCE TO RELATED APPLICATION

This application is a Division of prior application, Ser. No. 07/816,425, filed Dec. 31, 1991, now U.S. Pat. No. 5,259,986.

FIELD OF THE INVENTION

This invention relates to a process for the separation and recovery of unsaturated aliphatic hydrocarbons from a mixture of unsaturated aliphatic hydrocarbons and saturated aliphatic hydrocarbons.

In another aspect, this invention relates to a novel composition useful as an unsaturated aliphatic hydrocarbon complexing reagent, and a method of preparation therefor.

BACKGROUND OF THE INVENTION

A separations problem which has required and received considerable attention is that of separating unsaturated aliphatic hydrocarbons such as olefins from close boiling and difficulty separable saturated aliphatic hydrocarbons such as paraffins. Many processes have been proposed for such separations including liquid-liquid extraction, extractive distillation, as well as complex formation. With respect to complex formation, various complexing reagents have been described in the prior art. However, difficulties exist with the previously known systems. For example, aqueous systems involving copper (I), hereinafter denoted as (Cu(I)), salts and ammonia or ammonium are corrosive and lack necessary long term stability. Non-aqueous Cu(I) solutions using a pyridine solvent have proven difficult to handle due to the solvent and require large scale systems because the reagent is in the form of a slurry in the solvent. Cu(I) sulfonic acid reagents have proven too viscous for easy handling; furthermore the strong heats of absorption of these salts for olefins render the decomplexation difficult. Complexing reagents formed from Cu(I) salt and Lewis acid systems disclosed in the prior art have evidenced solubility problems and solvent alkylation problems.

Several examples of Lewis acid-free Cu(I) reagents are known. Prior art has disclosed a Cu(I) oxalate system and a Cu(I) fluorinated acetylacetonate system. Both of these systems, although active for ethylene complexation, possess enough drawbacks to render them unattractive for commercialization. The oxalate compound suffers from insufficient solubility while the acetylacetonate system appears to exhibit less than ideal stability in addition to high ligand cost.

There exists therefore, the need for a complexing reagent which has a high olefin complexing capacity while providing for easy desorption of the olefin, has a high solubility in an inert solvent, has a favorable viscosity, is relatively stable, gives few side reactions during the complexing process, and can be prepared from cheap starting materials.

It is an object of this invention to provide complexing agents for separation of olefins from paraffins which exhibit good olefin complexing capacity and easy reversibility, and are soluble in inert solvents.

It is also an object of this invention to provide a method for preparing such complexing reagents from relatively inexpensive starting materials.

It is also an object of this invention to provide a method for separating olefins from a mixture of olefins and paraffins by using the aforementioned complexing reagents.

SUMMARY OF THE INVENTION

In accordance with this invention, it has been discovered that complexing reagents comprising Cu(I) carboxylates and/or Cu(I) sulfonates associated with a high molecular weight olefin are useful for separating olefins from olefin and paraffin mixtures. It has further been discovered that the addition of the high molecular weight olefin enhances the solubility of the complexing reagent in an aromatic solvent, and renders the complexing reagent more stable. The complexing reagents of this invention exhibit the desirable properties of high capacity for olefin adsorption, low viscosity, easy reversibility and absence of side reactions.

In accordance with this invention, a complexing reagent is prepared by contacting a Cu(I) carboxylate or Cu(I) sulfonate with a high molecular weight olefin having about 10 to about 20 carbon atoms.

Further in accordance with this invention, olefins are separated from a mixture of olefins and paraffins by contacting the mixture with a complexing reagent comprising a Cu(I) carboxylate or Cu(I) sulfonate associated with a high molecular weight olefin having about 10 to about 20 carbon atoms under conditions such that the olefin forms a olefin/reagent complex while the paraffins remain uncomplexed. Thereafter, the olefin reagent is treated in order to separate the olefin from the complexing reagent.

DESCRIPTION OF THE PREFERRED EMBODIMENTS

Figure 1:
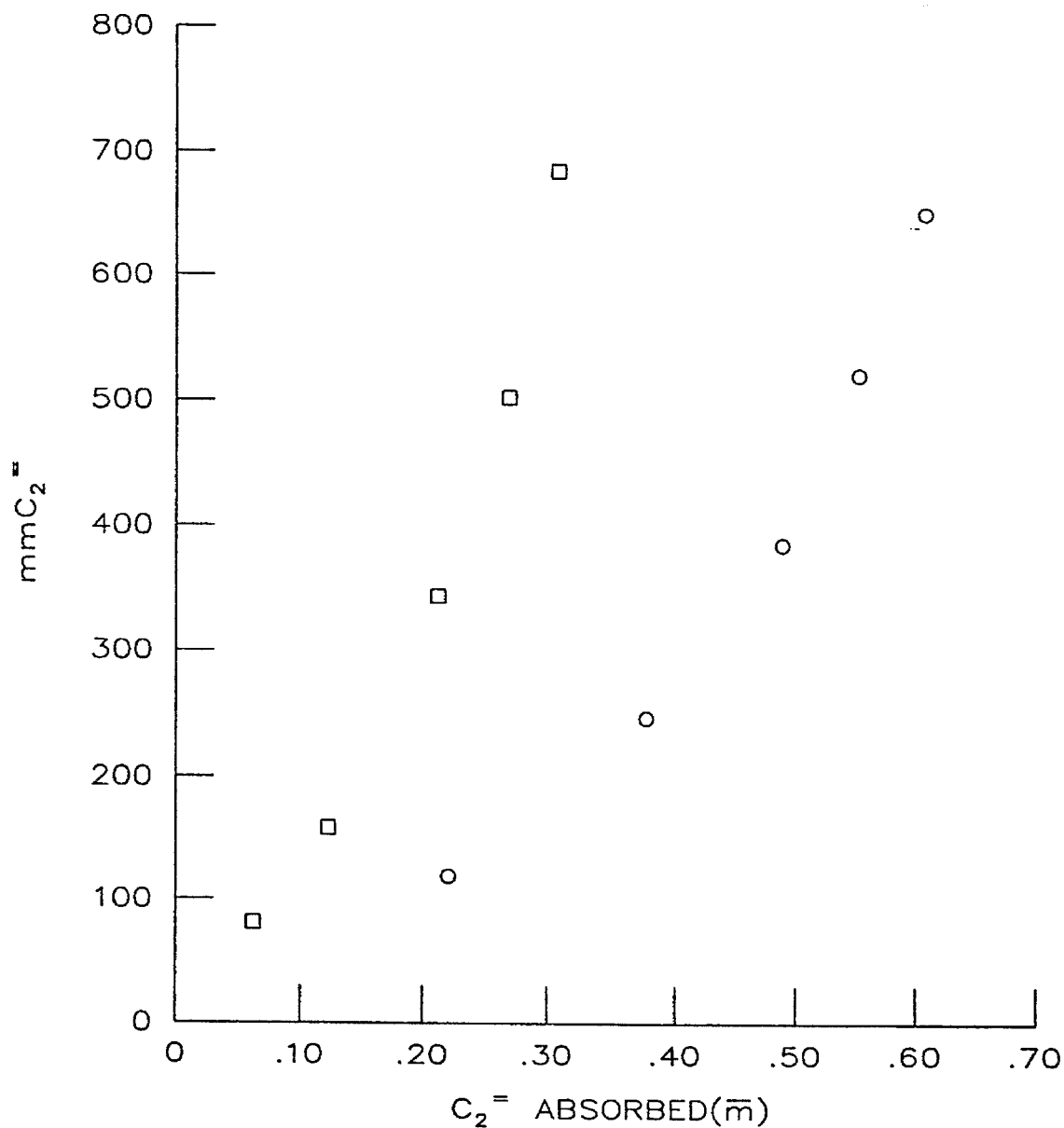
FIG. 1 depicts ethylene absorption curves for the invention complexing reagent and a comparative complexing reagent.

The Cu(I) carboxylates useful in this invention are the Cu(I) salts of mono-, di-, and tri-carboxylic acids containing 1 to about 20 carbon atoms. The carboxylic acid component of the salt can be aliphatic and/or have cyclic or aryl constituents. Suitable examples of Cu(I) carboxylates include but are not limited to Cu(I) formate, Cu(I) acetate, Cu(I) propionate, Cu(I) butyrate, Cu(I) pentanoate, Cu(I) hexanoate, Cu(I) octanoate, Cu(I) decanoate, Cu(I) methyl formate, Cu(I) ethyl acetate, Cu(I) n-propyl acetate, Cu(I) n-butyl acetate, Cu(I) ethyl propanoate, Cu(I) 2-ethyl hexanoate (Cu(I) octoate), Cu(I) benzoate, and Cu(I) p-t-butyl benzoate. The preferred Cu(I) carboxylate for use in this invention is Cu(I) 2-ethyl hexanoate due to its high solubility in hydrocarbon solvents. The copper (I) carboxylates can be prepared in any manner known to those skilled in the art, such as, for example by contacting the corresponding Cu(II) carboxylate with copper powder in an aromatic solvent under a carbon monoxide atmosphere, with a provision for removing any water of reaction or other undesired byproducts. In a preferred embodiment, the Cu(I) carboxylate is prepared by contacting Cu(II) acetate with the carboxylic acid which corresponds to the desired Cu(I) carboxylate product in an aromatic solvent, then subsequently reacting with copper powder under a reducing atmosphere. Again, provision should be made for removing water of reaction or other undesired byproducts. The initial reaction should be carried out under an oxygen-free inert atmosphere such as nitrogen and in the essential absence of water. The reducing atmosphere is preferably carbon monoxide, but those of ordinary skill in the art can easily substitute other reducing atmospheres if desired. Otherwise, a commercially obtained Cu(I) carboxylate can be used directly in the preparation of the complexing reagent.

The Cu(I) sulfonates useful in this invention are the Cu(I) salts of sulfonic acids having 4 to 22 carbon atoms. The sulfonic acid component of the salt can be aliphatic and/or have cyclic or aryl constituents. The aliphatic sulfonic acids useful in the practice of this invention can be straight chain or branched. Examples of suitable aliphatic sulfonic acids include n-butanesulfonic acid, 2-ethyl-1-hexanesulfonic acid, 2-methylnonanesulfonic acid, dodecanesulfonic acid, 2-ethyl-5-n-pentyltridecanesulfonic acid, n-eicosanesulfonic acid, and the like.

The aromatic sulfonic acids useful in the practice of this invention include benzenesulfonic acid, alkylbenzenesulfonic acids wherein the alkyl member contains from 1 to 16 carbon atoms, such as p-toluenesulfonic acid, p-dodecylbenzenesulfonic acid, p-hexadecylbenzenesulfonic acid, and the like, naphthalenesulfonic acid, phenolsulfonic acid, naphtholsulfonic acids, and halobenzenesulfonic acids, such as p-chlorobenzenesulfonic acid, p-bromobenzenesulfonic acid, and the like. A presently preferred aromatic sulfonic acid is p-dodecylbenzenesulfonic acid. Commercially available mixtures of o-, m-, and p-dodecylbenzenesulfonic acid can be employed.

Also useful in this invention are petroleum sulfonic acids which can be prepared from a deasphalted, solvent-refined petroleum fraction having a viscosity of about 140 to about 720 SUS at 210° F. (99° C.).

The complexing reagent is generally prepared by contacting the Cu(I) carboxylate or sulfonate with a high molecular weight olefin. It is preferred to contact the carboxylate and high molecular weight olefin in an aromatic solvent. The preparation is carried out under an oxygen-free inert atmosphere such as nitrogen and in the essential absence of water.

The high molecular weight olefins useful in this invention are those having about 10 to about 20 carbon atoms. Suitable examples include decene, undecene, dodecene, tridecene, tetradecene, pentadecene, neodene, propylene tetramer, eicosene, and the like. Preferred high molecular weight olefins are propylene tetramer and neodene.

The high molecular weight olefin is generally employed in an amount sufficient to substantially solubilize the Cu(I) carboxylate or sulfonate or reduce the viscosity of the complexing reagent solution to an acceptable level.

The Cu(I) carboxylate or sulfonate is generally employed in the complexing reagent solution in a concentration in the range of about 0.005 to 3 molar. It is desirable to have as much of the Cu(I) carboxylate or sulfonate in the solution as can be made soluble by contacting with the high molecular weight olefin, but at the same time, increased concentrations of Cu(I) carboxylate or sulfonate increase solution viscosity; greater solution viscosity can cause pumping and processing difficulties and is to be avoided if possible. Cu(I) carboxylate or sulfonate concentrations in the range of about 0.01 to about 2 molar have given highly satisfactory results and are therefore preferred.

The aromatic solvents useful in this invention are hydrocarbons with unsubstituted or alkyl substituted aryl groups, which are normally in the liquid phase under ambient conditions. Suitable examples include toluene, xylene, and the like. The aromatic solvent most preferred is xylene.

The process of the invention is advantageously employed for the separation of mixtures of close boiling aliphatic hydrocarbons having from 2 to about 25 carbon atoms, preferably from 2 to about 10 carbon atoms. Such separations include the separation of olefin hydrocarbons from paraffin and/or naphthene hydrocarbons and the separation of diolefin hydrocarbons from paraffin and/or naphthene hydrocarbons. The process of the invention is particularly suitable for separating aliphatic monoolefins from close boiling saturated hydrocarbons. The process is often utilized for the separation of normally gaseous olefins having from 2–4 carbon atoms from paraffins and the separation of olefins and cycloolefins having from 5–7 carbon atoms from paraffins.

It is also within the scope of this invention to perform a separation of heavier olefins and paraffins which are typically soluble in organic solvents, by choosing an organic solvent in which the olefin/reagent complex is relatively insoluble.

Acyclic and cyclic olefins having from 2 to about 20 carbon atoms per molecule can be separated from paraffins and cycloparaffins by employing the reagent of the invention. Examples include ethylene, propylene, the butenes, 2-pentene, cyclopentene, cyclohexene, cycloheptene, 1-heptene, 1-dodecene, 1-eicosene, 3-methyl-1-butene, 4-methyl-1-pentene, 2,3-dimethyl-2-butene, and the like.

The type of separation contemplated in this invention is the separation of alkenes and cycloalkenes from a paraffin or several paraffins, all components of the mixture having similar boiling points. Examples include the separation of ethylene from ethane, propylene from propane, 1-octene from n-octane, cyclohexene from cyclohexane, and the like.

The conditions employed in practicing this invention are selected to allow the olefin to react with the complexing reagent to form the complex while minimizing the problem of separating the nonreacted or noncomplexed portion of the feedstream. In the absorption zone, an absolute pressure ranging from about 0.05 to 20 atmospheres (0.005 to 2 MPa), more preferably from about 0.05 to 2 atmospheres (0.005 to 0.2 MPa), and a temperature ranging from about $-10°$ C. to about $10°$ C. below the boiling point of the solution of the complexing reagent, preferably from about $30°$ C. to about $25°$ C. below the boiling point of the solution of the complexing reagent, can be used.

In the desorption zone, the conditions are selected sufficiently different from those used in the absorption zone to promote desorption. Thus, an absolute pressure ranging from about 0.1 to 1.5 atmospheres (0.01 to 0.15 MPa), more preferably from about 0.5 to 1 atmosphere (0.05 to 0.1 MPa), can be employed. The temperature in this zone can range from about $50°$ C. below the boiling point of the solution of the reagent to the boiling point of the solution, more preferably from about $30°$ C. below the boiling point of the solution of the reagent to the boiling point of the solution.

The following examples are meant to illustrate the invention and should not be taken to limit the scope thereof.

The complexing reagents were tested in a pressure swing olefin absorption apparatus.

EXAMPLE I

This example describes the preparation of a Cu(I) octoate complexing agent wherein the starting material is a CD(II) octoate.

A 10 g sample of anhydrous Cu(II) octoate (0.028 moles) from Shepherd Chemical Company, 150 cc toluene and 3.6 g (0.0567 moles) Cu powder was added to a 300 cc autoclave. The autoclave was flushed with carbon monoxide (CO) gas and pressurized to 750 psig. No apparent reaction (indicated by CO uptake) occurred after 30 minutes at room temperature so the temperature was increased to 140° C. At this temperature CO uptake was observed in the form of pressure decreases and when no further CO uptake occurred, the autoclave was cooled to room temperature. A sample aspirated out of the vessel revealed a partially soluble light blue solid. The solid was air sensitive, turning blue-green almost immediately upon exposure to air. Addition of water to a portion of the sample brought about immediate $Cu°$ metal formation and a dark blue solution, believed to be due to disproportionation. The Cu(I) octoate formed by the reaction above was soluble in the xylene while in the autoclave, but upon carbon monoxide loss became only partially soluble. Thus, upon removal of the Cu(I) octoate from the autoclave, a slurry was formed which was stored under a nitrogen atmosphere until further use.

A second preparation of Cu(I) octoate was performed in a manner similar to that described above except that 17.5 g Cu(II) octoate, 6.3 g Cu powder and 100 cc xylene were used. Again, upon removal of the Cu(I) octoate in xylene from the autoclave, a slurry was formed.

Upon testing in the ethylene absorption apparatus, the Cu(I) octoate in the xylene slurry complexed with the ethylene in a 1:1 ratio and became soluble in the xylene solvent. Upon decomplexation, a slurry was again formed.

According to this invention, neodene was added to the Cu(I) octoate/xylene slurry. Upon addition of the neodene, the Cu(I) octoate was solubilized, resulting in a transparent light blue solution.

The solution was tested in the ethylene absorption apparatus and was found to be active for olefin complexation. As can be seen in FIG. 1 the invention complexing reagent solution containing the high molecular weight olefin did not effectively complex as much ethylene as the complexing reagent slurry; however, it is considered that the solution form of the invention complexing reagent is more desirable than a slurry complexing agent.

EXAMPLE II

Figure 2:
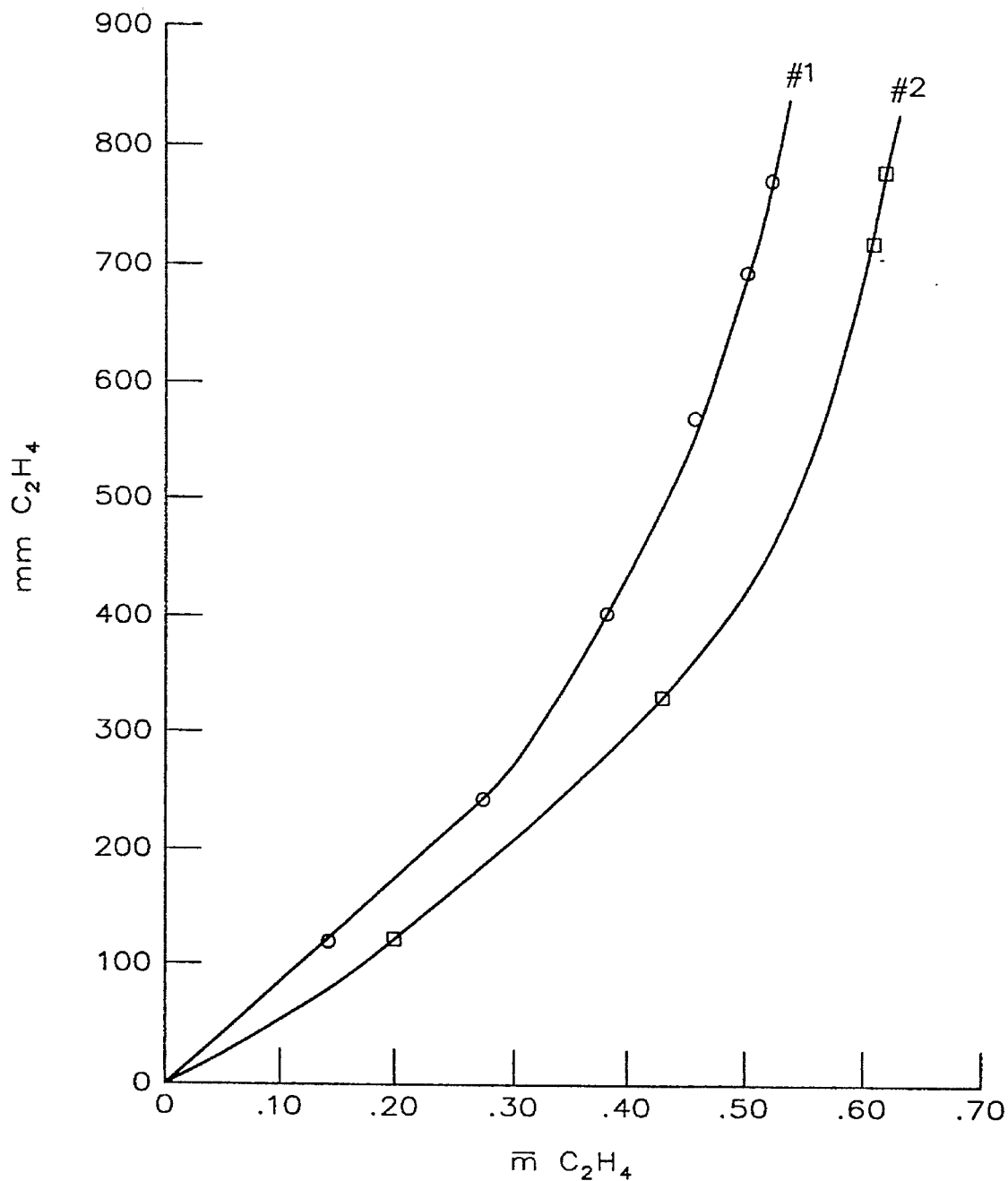
FIGS. 2 and 3 depict ethylene absorption curves for the invention complexing reagents.

A Cu(I) octoate complexing reagent was prepared by reacting Cu(II) acetate hydrate (10 g) with 2-ethyl-hexanoic acid (14.4 g) in 200 cc toluene to form Cu(II) octoate; then refluxing the Cu(II) octoate with 3.7 g Cu powder and 100 cc acetonitrile for 1 hour. At the end of the hour, approximately 50 mL solvent remained in the flask; the Cu(I) octoate was in the form of a slurry in the solvent. Then, 50 mL of propylene tetramer was added to the flask. The remaining toluene and acetonitrile were evaporated along with a small portion of the propylene tetramer. Thereafter, 50 cc propylene tetramer was added. The Cu(I) octoate appeared to be completely soluble in the propylene tetramer. A 10 mL sample of the Cu(I) octoate/propylene tetramer complexing reagent was tested in the ethylene absorption apparatus. The absorption curve is depicted in FIG. 2 as curve #1.

A second complexing reagent was prepared as a 1 $\overline{m}$ solution of Cu(I) octoate in 5 mL xylene and 5 mL propylene tetramer. This complexing reagent was also tested in the ethylene absorption apparatus and the resulting absorption curve is depicted in FIG. 2 as curve #2.

The Cu(I) octoate in 50% xylene/50% propylene tetramer complexing reagent was slightly more active for ethylene complexation than the Cu(I) octoate/propylene tetramer.

EXAMPLE III

Three complexing reagent solutions containing Cu(I) dodecyl benzene sulfonate (Cu(I) dobanate) were prepared and tested in the ethylene absorption apparatus.

Solution 1 was prepared as a 1 $\overline{m}$ solution of Cu(I) dobanate in 10 mL of octene-1. Solution 2 was prepared as a 1 $\overline{m}$ solution of Cu(I) dobanate in a mixture of 5 mL xylene and 5 mL octene-1. Solution 3 was prepared as a 1 m solution of Cu(I) dobanate in 10 mL xylene.

Figure 3:
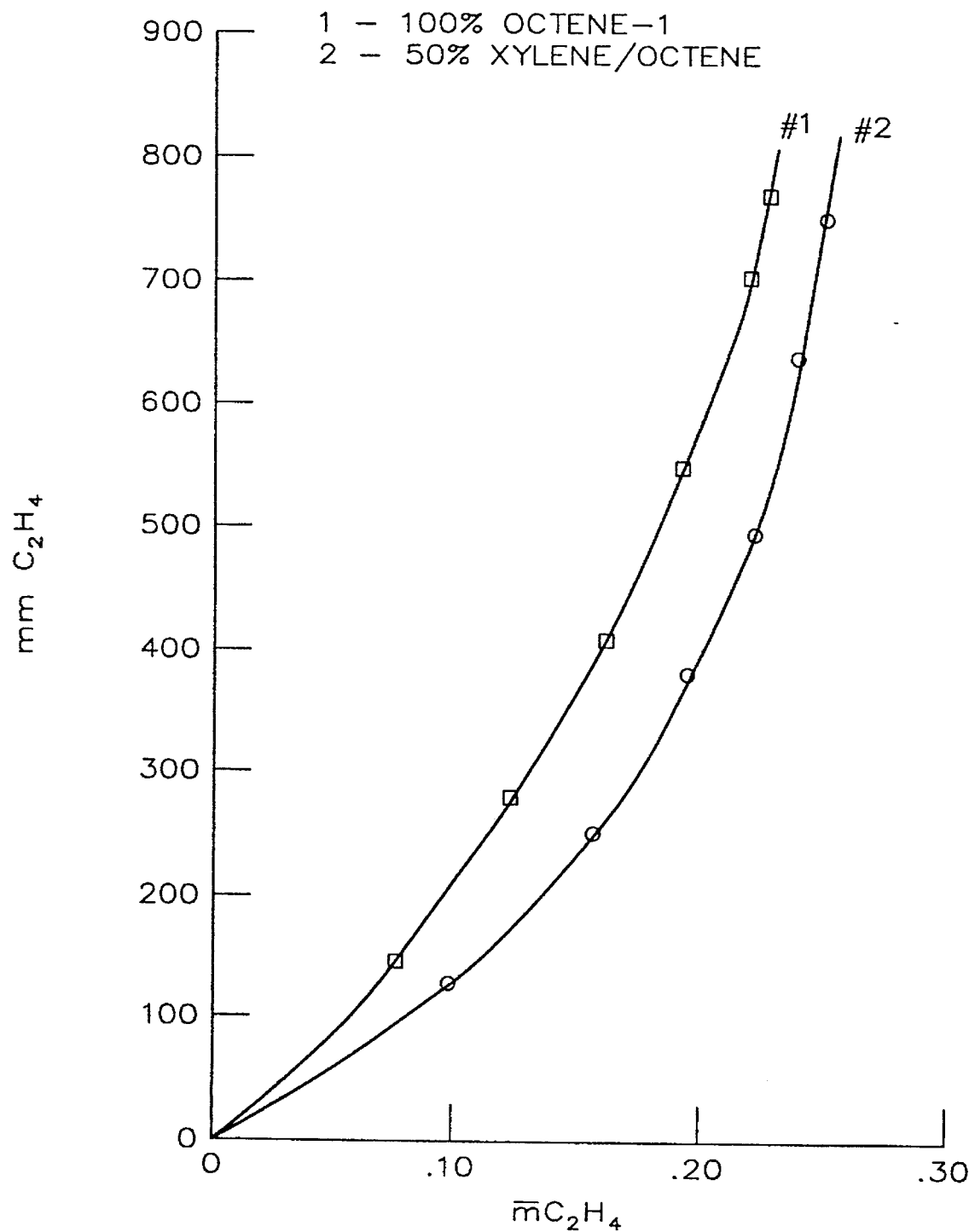
Figure 4:
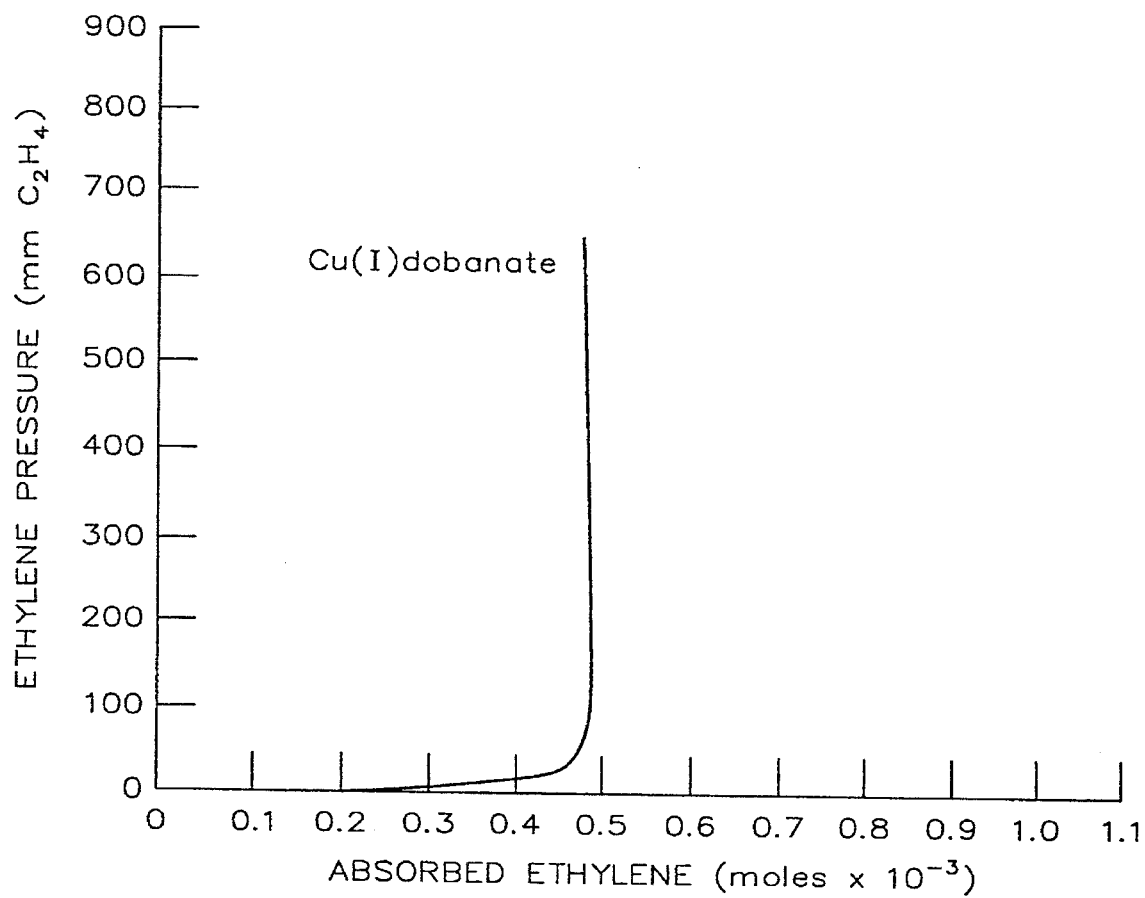
FIG. 4 depicts an ethylene absorption curve for a comparative complexing reagent.

FIG. 3 depicts the absorption curves for Solutions 1 and 2, FIG. 4 depicts the absorption curve for Solution 3. The Cu(I) dobanate in xylene solution (FIG. 4) exhibits the behavior of a strong complex between the reagent and the ethylene and therefore requires more energy to remove the olefin from the complex. FIG. 3 demonstrates that the Cu(I) dobanate associated with the high molecular weight olefin forms a much weaker complex with the ethylene. The Cu(I) dobanate in xylene and octene-1 exhibited a higher capacity for ethylene complexation while still maintaining the characteristics of a weak complex. Thus, while the Cu(I) dobanate/high molecular weight olefin complexing reagents have a lower capacity for ethylene absorption than the Cu(I) dobanate in xylene reagent, less energy is required to remove the ethylene from the invention complexing reagent/ olefin complex.

While this invention has been described in detail for the purpose of illustration, it is not to be construed as limited thereby, but is intended to cover all changes and modifications within the spirit and scope thereof.

That which is claimed is:

1. A process for separating a low molecular weight olefin from admixture with paraffins comprising the steps of
    a) contacting said admixture under an inert atmosphere with a complexing reagent solution comprising a copper (I) carboxylate and a high molecular weight olefin having about 10 to about 20 carbon atoms, whereby said low molecular weight olefin forms a substantially soluble olefin/reagent complex while said paraffins remain insoluble;
    b) separating said substantially soluble olefin/reagent complex from said insoluble paraffins; and
    c) recovering said low molecular weight olefin from said substantially soluble olefin/reagent complex.

2. A process in accordance with claim 1 wherein said copper (I) carboxylate is present in said complexing reagent solution in an amount in the range of about 0.005 to about 3 molar.

3. A process in accordance with claim 1 wherein said complexing reagent solution further comprises an aromatic solvent.

4. A process in accordance with claim 1 wherein said low molecular weight olefin complexed is ethylene.

5. A process in accordance with claim 1 wherein said copper (I) carboxylate is copper (I) 2-ethylhexanoate.

* * * * *